(12) United States Patent
Ward et al.

(10) Patent No.: US 9,822,219 B2
(45) Date of Patent: Nov. 21, 2017

(54) MULTIFUNCTIONAL BENZOXAZINES AND COMPOSITE MATERIALS INCORPORATING THE SAME

(71) Applicant: Cytec Industries Inc., Woodland Park, NJ (US)

(72) Inventors: Steven Richard Ward, Stockton-on-Tees (GB); Paul Mark Cross, York (GB)

(73) Assignee: CYTEC INDUSTRIES INC., Woodland Park, NJ (US)

( * ) Notice: Subject to any disclaimer, the term of this patent is extended or adjusted under 35 U.S.C. 154(b) by 382 days.

(21) Appl. No.: 14/562,799

(22) Filed: Dec. 8, 2014

(65) Prior Publication Data

US 2015/0175746 A1    Jun. 25, 2015

(30) Foreign Application Priority Data

Dec. 20, 2013   (GB) .................................. 1322758.2

(51) Int. Cl.
| | |
|---|---|
| *C08G 73/02* | (2006.01) |
| *D06M 15/61* | (2006.01) |
| *C08K 5/357* | (2006.01) |
| *C07D 265/16* | (2006.01) |

(52) U.S. Cl.
CPC ....... *C08G 73/0233* (2013.01); *C07D 265/16* (2013.01); *C08K 5/357* (2013.01); *D06M 15/61* (2013.01); *Y10T 428/249921* (2015.04)

(58) Field of Classification Search
CPC .. C08G 73/0266; C08G 73/06; C07D 265/16; C08K 5/357
USPC ........... 428/506; 442/161, 252; 528/86, 129, 528/153, 162, 163, 219
See application file for complete search history.

(56) References Cited

U.S. PATENT DOCUMENTS

| | | | |
|---|---|---|---|
| 8,148,028 B2 | 4/2012 | Choi et al. | |
| 2009/0270615 A1 | 10/2009 | Taden et al. | |
| 2013/0345352 A1* | 12/2013 | Ward ................. | C08G 73/0233 524/413 |

OTHER PUBLICATIONS

Lin, C., Synthesis and properties of flame-retardant benzoxazines by three approaches. J. Polym. Sci. A Polym. Chem., 44: 3454-3468. doi:10.1002/pola.21454, 2006.*

* cited by examiner

Primary Examiner — Frank Vineis
(74) Attorney, Agent, or Firm — Thi Dang

(57) ABSTRACT

A curable resin composition containing a blend of multifunctional benzoxazines, and composite materials derived therefrom. The benzoxazine blend contains the combination of (A) a difunctional benzoxazine component and (B) a multifunctional benzoxazine component with functionality of greater than 2. Cured matrix resins and cured composite materials containing such benzoxazine blend exhibit a significant retardation in the rate of organic solvent uptake as compared to the same cured matrix resins and composite materials without component (B).

19 Claims, 4 Drawing Sheets

MULTIFUNCTIONAL BENZOXAZINES AND COMPOSITE MATERIALS INCORPORATING THE SAME

This application claims the benefit of prior United Kingdom Patent Application No. 1322758.2, filed on Dec. 20, 2013.

BACKGROUND

The use of benzoxazines (BOX) offers a number of advantages as compared to other thermosetting resins including relatively long shelf-life, molecular design flexibility, low cost, high glass transition temperature ($T_g$), high modulus, relatively low viscosities, good flame retardant properties, low moisture absorption, no by-products released during curing and very low shrinkage upon curing. Furthermore, benzoxazines are capable of being self-cured upon heating; i.e. there is no need for an additional curing agent. This combination of properties means benzoxazines are potentially attractive for use in aerospace applications.

The commercial use of pure benzoxazine matrices in high-performance composites is currently not well established. Several commercial systems of benzoxazine hybrid systems are available (usually benzoxazine-epoxy) but the epoxy negates some of the benefits brought by benzoxazines. Toughening of benzoxazine only systems was limited to the use of rubbers, modified benzoxazine monomers and low performance thermoplastics, but these also reduce the beneficial properties of benzoxazines, most notably the flexural and tensile modulus.

SUMMARY

Disclosed herein are blends of multifunctional benzoxazines, curable compositions containing such blends, cured matrix resins derived therefrom, and composite materials containing the blends. The blends and curable compositions are based on the combination of a difunctional benzoxazine component and a multifunctional benzoxazine component with functionality of greater than 2, particularly, benzoxazines with average functionality from 2.1 to 3.

Cured matrix resins and cured composite materials containing blends of di-functional and multi-functional benzoxazines exhibit a significant retardation in the rate of organic solvent uptake.

DETAILED DESCRIPTION

Figure 1:
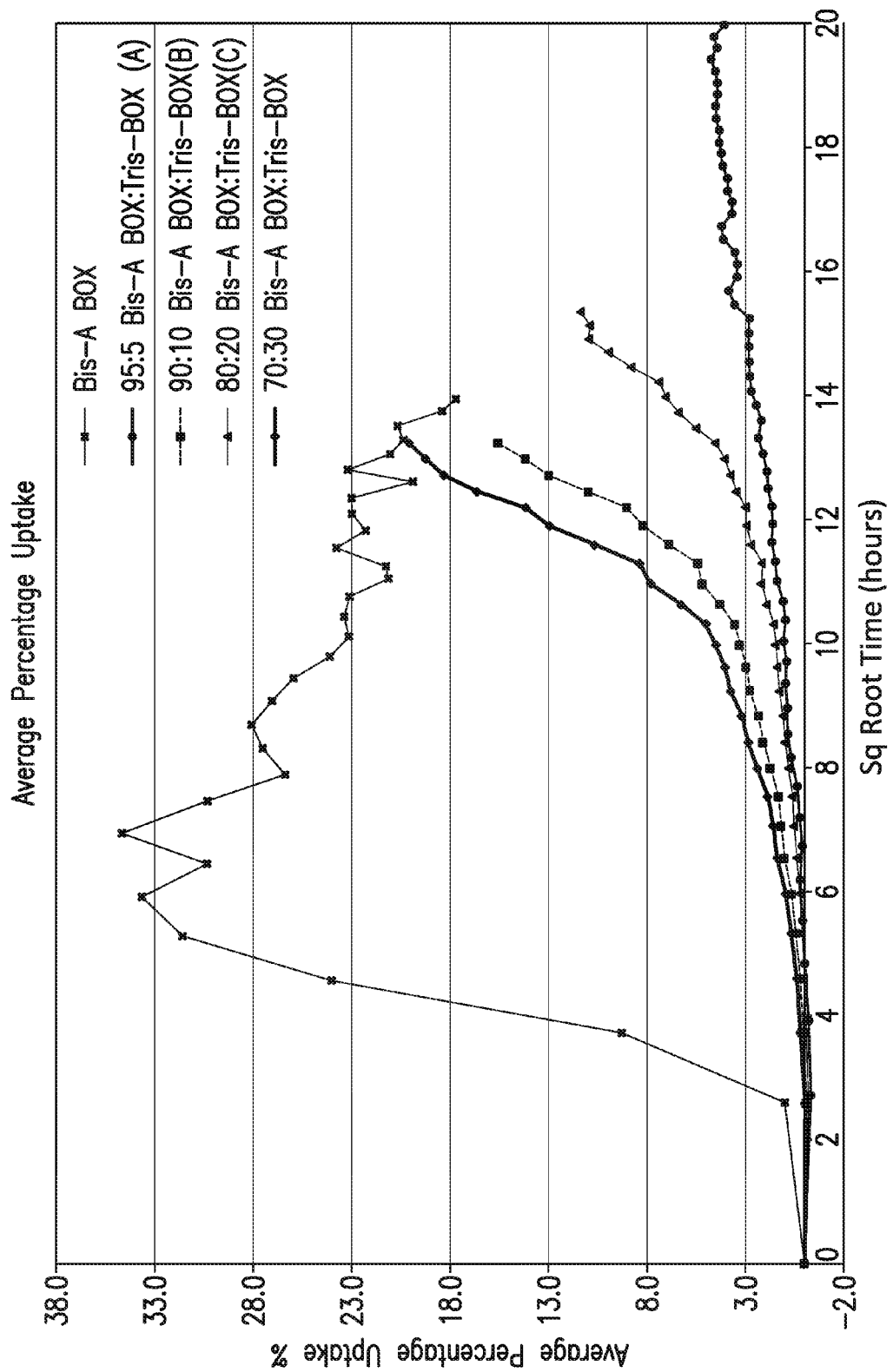
FIG. 1 shows the rate of solvent uptake for different benzoxazine blends prepared in an example.

Benzoxazine resins are known to be very resistant to water uptake, commonly uptaking <2% at saturation. This benefit allows them to have a low differential between their (higher) dry $T_g$ and (lower) wet $T_g$, meaning that their usage temperature can be higher than, for example, epoxy resins or benzoxazine-epoxy hybrids with comparable dry $T_g$.

Benzoxazines have been known to have extremely good solvent resistance with reports for MEK uptake at room temperature to be <0.2% after a 7-month MEK soak. MEK resistance tests are critical as they are used by most aerospace composite manufacturers as part of their design criteria. Surprisingly, it has been found that, in boiling MEK, the uptake in a neat benzoxazine could be >23% in just 16 hrs. This was not the case for a benzoxazine-epoxy hybrid system, which took up approximately 2.5% after 190 hrs.

Although the benzoxazine-epoxy hybrid systems have a good balance of properties, they do not possess the extremely high flexural modulus of the neat benzoxazine systems (i.e 100% benzoxazine). This discovery offers the potential to utilise neat benzoxazine resin systems in aerospace composites by mitigating a potential resin failing. An alternative strategy to address this failing could have been to formulate a more hydrophilic component into the formulation. However, the risk would have been a damaging uptake in water absorption. A major benefit of the approach taken is reflected in the fact that there is a very minor effect on water uptake in these neat benzoxazines. The level of uptake is increased on addition of 30% multifunctional benzoxazine but still remains below 1.6% at equilibrium.

It has been discovered that reduced solvent uptake may be achieved for a cured benzoxazine-based resin when the resin composition contains a blend of (A) a di-functional benzoxazine component and (B) a multifunctional benzoxazine component with an average functionality of >2, particularly, benzoxazines with an average functionality of about 2.1 up to about 3. The retardation in solvent uptake (e.g. MEK) has been found to be significant as compared to the same cured benzoxazine resin without component (B).

In a benzoxazine blend, the multifunctional benzoxazine component may be present in an amount of up to 30% by weight based on the total weight of the benzoxazine blend. According to one embodiment, the weight ratio of multifunctional benzoxazine component (B) to difunctional benzoxazine component (A) may be in the range of 1:99 to 30:70.

The multifunctional benzoxazines (or polybenzoxazines), as disclosed herein, refer to polymerizable benzoxazine compounds with at least two oxazine moieties in the compound, enabling the formation of crosslinks. More specifically, difunctional benzoxazine contains two oxazine moieties, and tri-functional benzoxazine contains three oxazine moieties. Blends of benzoxazines with non-integer average functionalities (e.g. 2.1, 2.2, 2.3, 2.4, 2.5, etc.) can be formed as a consequence of incomplete reaction during synthesis or ring opening of integer functional molecules or through blending molecules with integer functionalities. For example, a combination of molecules with two oxazine moieties and molecules with three oxazine moieties would yield a benzoxazine component with an average functionality of between 2 and 3. The multifunctional benzoxazine compounds in the blends include multifunctional monomers and oligomers that can be polymerized by curing to form a thermoset resin.

Upon curing, the multifunctional benzoxazine compounds readily polymerize via ring opening polymerization. Such polymerization is usually initiated cationically (using cationic initiators) or thermally.

Cured matrix resins resulting from curing blends of di-functional and multifunctional benzoxazines with average functionality of greater than 2 (or >2), exhibits a retardation in the rate of organic solvent uptake, e.g. methyl ethyl ketone (MEK).

The solvent in the context of solvent uptake includes organic solvents such as MEK. This effect would be expected to be observed to a greater or lesser extent in benzoxazine hybrid systems (e.g. benzoxazine-epoxy systems). Neat or pure (100%) benzoxazine system in this context refers to a benzoxazine-based composition which is void of any other curable/thermosettable resin such as epoxy, cyanate ester, BMI and phenolic/phenol-formaldehyde resins but may include catalysts/initiators, toughening agents or functional additives. Examples of such functional additives include, but are not limited to, fillers, color pigments, rheology control agents, tackifiers, conductive additives, flame retardants, ultraviolet (UV) protectors, and the like. These additives may take the form of various geometries including, but are not limited to, particles, flakes, rods, and the like.

When one or more multifunctional benzoxazines with average functionality >2 are blended with di-functional benzoxazines such as Bisphenol-A benzoxazine, the effect in reducing MEK uptake is such that it could be used at levels as low as 1 wt % based on the weight of the resin formulation. In the case of a multifunctional benzoxazine with an average functionality of 2.5, its inclusion increases the time taken to reach 3% MEK uptake from approximately 9 hours for pure Bisphenol-A benzoxazine to 49 hours for a blend of 99:1 Bis-A benzoxazine:multifunctional benzoxazine. Such low levels of inclusion would not be expected to show significant mechanical property differences or deterioration of the cured resin.

Multifunctional Benzoxazines with Functionality >2

The multifunctional benzoxazine component discussed above includes one or more multifunctional benzoxazines having functionality of >2, including tri-functional benzoxazines represented by the following generic structure I:

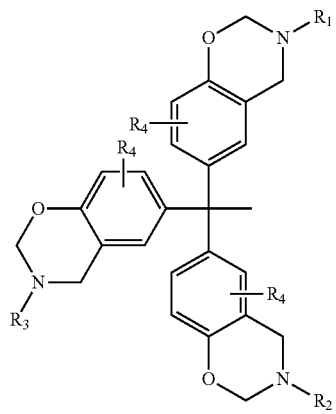

(I)

where $R_1$, $R_2$ and $R_3$ are independently selected from alkyl (preferably $C_{1-8}$ alkyl), cycloalkyl (preferably $C_{5-7}$ cycloalkyl, particularly $C_6$ cycloalkyl), and aryl, wherein the cycloalkyl and aryl groups are optionally substituted, for instance by $C_{1-8}$ alkyl, halogen and amine groups, and preferably by $C_{1-8}$ alkyl, and where substituted, one or more substituent groups (preferably one substituent group) may be present on each cycloalkyl and aryl group; $R_4$ is selected from hydrogen, halogen, alkyl and alkenyl.

According to a preferred embodiment, the tri-functional benzoxazine is represented by the following structure II:

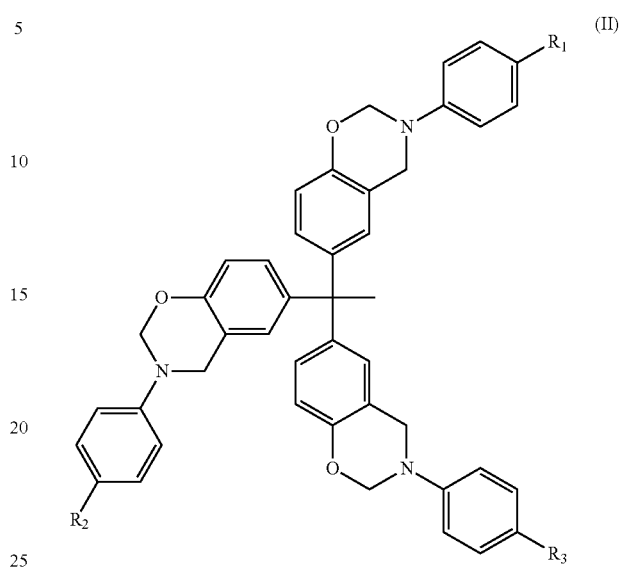

(II)

where $R_1$, $R_2$ and $R_3$ are independently selected from alkyl (preferably $C_{1-8}$ alkyl).

A specific example of a suitable tri-functional benzoxazine is:

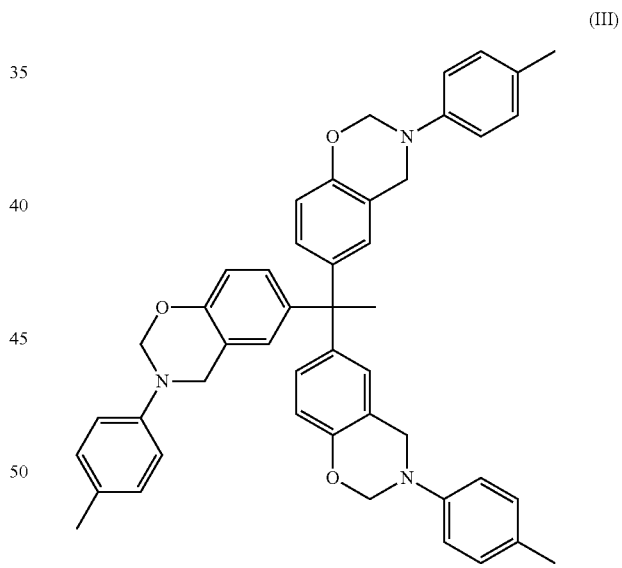

(III)

The multifunctional benzoxazine component with functionality >2 may be a reaction product of a trihydric phenol (or tris-phenol), an aromatic amine, and formaldehyde. A particularly suitable tris-phenol is 1,1,1-tris(4-hydroxyphenyl)ethane. According to one specific example, the multifunctional benzoxazine component is a reaction product of 1,1,1-tris(4-hydroxyphenyl)ethane, p-toluidine, and p-formaldehyde.

An additional example of benzoxazines with functionality >2 would be a blend of the above tri-functional structure I, II or III and a similar structure with only two completely closed oxazine moieties, the final phenol being either unreacted, partially reacted with formaldehyde or ring opened.

Difunctional Benzoxazines

The difunctional benzoxazine component may be include one or more benzoxazines represented by the following structure IV:

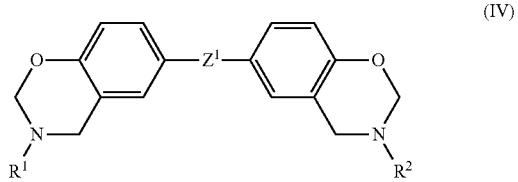

where $Z^1$ is selected from a direct bond, —C($R^3$)($R^4$)—, —C($R^3$)(aryl)-, —C(O)—, —S—, —O—, —S(O)—, —S(O)$_2$—, a divalent heterocycle and —[C($R^3$)($R^4$)]$_x$-arylene-[C($R^5$)($R^6$)]$_y$—, or the two benzyl rings of the benzoxazine moieties may be fused; and $R^1$ and $R^2$ are independently selected from alkyl (preferably $C_{1-8}$ alkyl), cycloalkyl (preferably $C_{5-7}$ cycloalkyl, preferably $C_6$ cycloalkyl) and aryl, wherein the cycloalkyl and aryl groups are optionally substituted, for instance by $C_{1-8}$ alkyl, halogen and amine groups, and preferably by $C_{1-8}$ alkyl, and where substituted, one or more substituent groups (preferably one substituent group) may be present on each cycloalkyl and aryl group;

in one embodiment, $Z^1$ is selected from a direct bond, —C($R^3$)($R^4$)—, —C($R^3$)(aryl)-, —C(O)—, —S—, —O—, a divalent heterocycle and —[C($R^3$)($R^4$)]$_x$-arylene-[C($R^5$)($R^6$)]$_y$—, or the two benzyl rings of the benzoxazine moieties may be fused;

$R^3$, $R^4$, $R^5$ and $R^6$ are independently selected from H, $C_{1-8}$ alkyl (preferably $C_{1-4}$ alkyl, and preferably methyl), and halogenated alkyl (wherein the halogen is typically chlorine or fluorine (preferably fluorine) and wherein the halogenated alkyl is preferably $CF_3$); and x and y are independently 0 or 1;

where $Z^1$ is selected from a divalent heterocycle, it is preferably 3,3-isobenzofuran-1(3h)-one, i.e. wherein the compound of formula (III) is derived from phenolphthalein;

where $Z^1$ is selected from —[C($R^3$)($R^4$)]$_x$-arylene-[C($R^5$)($R^6$)]$_y$—, then the chain linking the two benzoxazine groups may further comprise one or more arylene group(s) and/or one or more —C($R^7$)($R^8$)— group(s) where $R^7$ and $R^8$ are independently selected from the groups defined hereinabove for $R^3$.

In a preferred embodiment, the arylene group is phenylene. In one embodiment, the groups attached to the phenylene group may be configured in para- or meta-positions relative to each other. In a preferred embodiment, the aryl group is phenyl.

The group $Z_1$ may be linear or non-linear, and is typically linear. The group $Z_1$ is preferably bound to the benzyl group of each of the benzoxazine moieties at the para-position relative to the oxygen atom of the benzoxazine moieties, as shown in formula (I), and this is the preferred isomeric configuration. However, the group $Z_1$ may also be attached at either of the meta-positions or the ortho-position, in one or both of the benzyl group(s) in the bis-benzoxazine compound. Thus, the group $Z_1$ may be attached to the benzyl rings in a para/para; para/meta; para/ortho, meta/meta or ortho/meta configuration. In one embodiment, the difunctional benzoxazine resin component comprises a mixture of isomers, preferably wherein the major portion of the mixture is the para/para isomer shown in structure IV, and preferably this is present in at least 75 mol %, preferably at least 90 mol %, and preferably at least 99 mol %, of the total isomeric mixture.

In a preferred embodiment, the difunctional benzoxazine is selected from compounds wherein $Z^1$ is selected from —C($CH_3$)$_2$—, —$CH_2$— and 3,3-isobenzofuran-1(3H)-one, i.e. benzoxazine derivatives of bisphenol A, bisphenol F and phenolphthalein.

In another embodiment, the difunctional benzoxazine is selected from compounds wherein $R^1$ and $R^2$ are independently selected from aryl, preferably phenyl. In one embodiment, the aryl group may be substituted, preferably wherein the substituent(s) are selected from $C_{1-8}$ alkyl, and preferably wherein there is a single substituent present on at least one aryl group. $C_{1-8}$ alkyl includes linear and branched alkyl chains. Preferably, $R^1$ and $R^2$ are independently selected from unsubstituted aryl, preferably unsubstituted phenyl.

The benzyl ring in each benzoxazine group of the difunctional benzoxazine compounds defined herein may be independently substituted at any of the three available positions of each ring, and typically any optional substituent is present at the position ortho to the position of attachment of the $Z^1$ group. Preferably, however, the benzyl ring remains unsubstituted.

An alternative structure V for the difunctional benzoxazines is represented below:

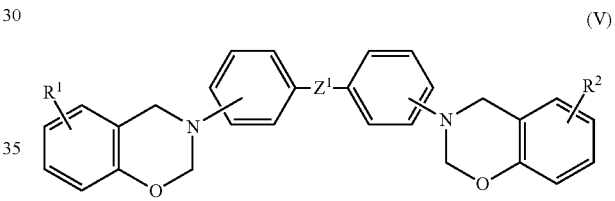

wherein $Z^1$ is selected from a direct bond, —C($R^3$)($R^4$)—, —C($R^3$)(aryl)-, —C(O)—, —S—, —O—, —S(O)—, —S(O)$_2$—, a divalent heterocycle and —[C($R^3$)($R^4$)]$_x$-arylene-[C($R^5$)($R^6$)]$_y$—, or the two benzyl rings may be fused; and $R^1$ and $R^2$ are independently selected from hydrogen, alkyl (preferably $C_{1-8}$ alkyl), cycloalkyl (preferably $C_{5-7}$ cycloalkyl, preferably $C_6$ cycloalkyl) and aryl, wherein the cycloalkyl and aryl groups are optionally substituted, for instance by $C_{1-8}$ alkyl, halogen and amine groups, and preferably by $C_{1-8}$ alkyl, and where substituted, one or more substituent groups (preferably one substituent group) may be present on each cycloalkyl and aryl group;

in one embodiment, $Z^1$ is selected from a direct bond, —C($R^3$)($R^4$)—, —C($R^3$)(aryl)-, —C(O)—, —S—, —O—, a divalent heterocycle and —[C($R^3$)($R^4$)]$_x$-arylene-[C($R^5$)($R^6$)]$_y$—, or the two benzyl rings may be fused;

$R^3$, $R^4$, $R^5$ and $R^6$ are independently selected from H, $C_{1-8}$ alkyl (preferably $C_{1-4}$ alkyl, and preferably methyl), and halogenated alkyl (wherein the halogen is typically chlorine or fluorine (preferably fluorine) and wherein the halogenated alkyl is preferably $CF_3$); and x and y are independently 0 or 1;

where $Z^1$ is selected from a divalent heterocycle, it is preferably 3,3-isobenzofuran-1(3h)-one, i.e. wherein the compound of formula (VII) is derived from phenolphthalein;

where $Z^1$ is selected from —[C($R^3$)($R^4$)]$_x$-arylene-[C($R^5$)($R^6$)]$_y$—, then the chain linking the two benzoxazine groups may further comprise one or more arylene group(s) and/or one or more —C($R^7$)($R^8$)— group(s) where $R^7$ and $R^8$ are independently selected from the groups defined hereinabove for $R^3$, provided that the or each substituted or unsubstituted methylene group is not adjacent to another substituted or unsubstituted methylene group.

In a preferred embodiment, the arylene group is phenylene. In one embodiment, the groups attached to the phenylene group may be configured in para- or meta-positions relative to each other. In a preferred embodiment, the aryl group is phenyl.

The group $Z_1$ may be linear or non-linear, and is typically linear. The group $Z_1$ may be attached at the meta-positions, the para-positions or the ortho-position, in one or both of the benzyl group(s) in the bis-benzoxazine compound. Thus, the group $Z_1$ may be attached to the benzyl rings in a para/para; para/meta; para/ortho, meta/meta or ortho/meta configuration. In one embodiment, the thermoset benzoxazine resin component (A) comprises a mixture of isomers, preferably wherein the major portion of the mixture is the para/para isomer shown in structure IV, and preferably this is present in at least 75 mol %, preferably at least 90 mol %, and preferably at least 99 mol %, of the total isomeric mixture.

In a preferred embodiment, the di-functional benzoxazine is selected from compounds wherein $Z^1$ is selected from —C($CH_3$)$_2$—, —$CH_2$— and 3,3-isobenzofuran-1(3H)-one In another embodiment, the difunctional benzoxazine is selected from compounds wherein $R^1$ and $R^2$ are independently selected from aryl, preferably phenyl. In one embodiment, the aryl group may be substituted, preferably wherein the substituent(s) are selected from $C_{1-8}$ alkyl, and preferably wherein there is a single substituent present on at least one aryl group. $C_{1-8}$ alkyl includes linear and branched alkyl chains. Preferably, $R^1$ and $R^2$ are independently selected from unsubstituted aryl, preferably unsubstituted phenyl.

The benzyl ring in the di-functional benzoxazine compounds defined herein may be independently substituted at any of the three available positions of each ring, and typically any optional substituent is present at the position ortho to the position of attachment of the $Z^1$ group. Preferably, however, the benzyl ring remains unsubstituted.

Curable Compositions and Application Thereof

The benzoxazine blend discussed above may be combined with additional components such as catalysts and toughening agents to form a curable composition suitable for the manufacture of resinous films (e.g. adhesive films, surfacing films) or fiber-reinforced composites (e.g. prepregs). The curable composition is a pure or 100% benzoxazine system which is void of any other curable/thermosettable resin(s) such as epoxy, cyanate ester, BMI and phenolic/phenol-formaldehyde resins. It is preferred that the total amount of all polymerizable benzoxazine compounds in the curable composition is greater than 80%, preferably 85%, by weight based on the total weight of the curable composition.

As used herein, a "curable composition" refers to a composition prior to curing and a "cured matrix resin" refers to a cured resin produced from curing the curable composition.

The addition of catalysts is optional, but the use of such may increase the cure rate and/or reduce the cure temperatures. Suitable catalysts for the benzoxazine-based composition include, but are not limited to, Lewis acids, such as phenols and derivatives thereof, strong acids, such as alkylenic acids, methyl tosylate, cyanate esters, p-toluenesulfonic acid, 2-ethyl-4-methylimidazole (EMI), 2,4-di-tert-butylphenol, $BF_3O(Et)_2$, adipic acid, organic acids, phosphorous pentachloride ($PCI_5$).

Toughening agents (or tougheners) may be added to produce a toughened matrix resin suitable for high-strength composites, such as those used in aerospace application. Suitable toughening agents include, but are not limited to, thermoplastic toughening agents such as polyethersulphone (PES), co-polymer of PES and polyetherethersulphone (PEES), elastomers, including liquid rubbers having reactive groups, particulate toughening agents such as thermoplastic particles, glass beads, rubber particles, and core-shell rubber particles.

Functional additives may also be included in the curable composition to influence one or more of mechanical, rheological, electrical, optical, chemical, flame resistance and/or thermal properties of the cured or uncured resin composition. Examples of such functional additives include, but are not limited to, fillers, color pigments, rheology control agents, tackifiers, conductive additives, flame retardants, ultraviolet (UV) protectors, and the like. These additives may take the form of various geometries including, but are not limited to, particles, flakes, rods, and the like.

If present, the total amount of other additives, including catalysts, toughener(s) and functional additive(s) is up to 15% by weight based on the total weight of the composition.

The curable composition as discussed above may be combined with reinforcement fibers to form a composite material or structure. Reinforcing fibers may take the form of whiskers, short fibers, continuous fibers, filaments, tows, bundles, sheets, plies, and combinations thereof. Continuous fibers may further adopt any of unidirectional, multi-directional, non-woven, woven, knitted, stitched, wound, and braided configurations, as well as swirl mat, felt mat, and chopped-fiber mat structures. The composition of the fibers may be varied to achieve the required properties for the final composite structure. Exemplary fiber materials may include, but are not limited to, glass, carbon, graphite, aramid, quartz, polyethylene, polyester, poly-p-phenylene-benzobisoxazole (PBO), boron, polyamide, graphite, silicon carbide, silicon nitride, and combinations thereof.

To form composite materials, the reinforcing fibers are impregnated or infused with the curable composition using conventional processing techniques such as, but not limited to prepregging and resin infusion. After resin impregnation/infusion, curing may be carried out at elevated temperature up to 230° C., preferably in the range of 160° C. to 230° C., more preferably at about 170° C.-230° C., and with the use of elevated pressure to restrain deforming effects of escaping gases, or to restrain void formation, suitably at pressure of up to 10 bar, preferably in the range of 3 to 7 bar absolute. The cure temperature may be attained by heating at up to 5° C./min, for example 2° C. to 3° C./min and is maintained for the required period of up to 9 hours, preferably up to 6 hours, for example 3 to 4 hours. Pressure is released throughout and temperature reduced by cooling at up to 5° C./min. for example up to 3° C./min. Post-curing at temperatures in the range of 190° C. to 230° C. may be performed, at atmospheric pressure, employing suitable heating rates to improve the glass transition temperature ($T_g$) of the product.

EXAMPLES

Described are the synthesis procedures for benzoxazines based on 1,1,1-tris(4-hydroxyphenyl)ethane, which is represented by the following chemical structure:

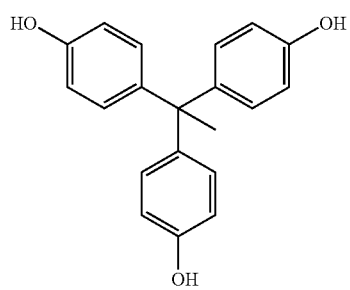 [SMILES: CC(c1ccc(O)cc1)(c1ccc(O)cc1)c1ccc(O)cc1]

Synthesis Procedures

1. Multifuctional Benzoxazine—Method A 1,1,1-Tris(4-hydroxyphenyl)ethane (60.00 g, 0.20 mol), p-formaldehyde (36.04 g, 1.2 mol) and p-toluidine (64.29 g, 0.60 mol) were combined in a jar with DMSO (150 cm$^3$) and placed in an oil bath at 85° C., equipped with overhead stirring. After 1 hour the temperature was raised to 130° C. for a further 3 hours. The crude melt was then poured directly into cold IPA (600 cm$^3$ at −78.5° C.) and stirred for 30 minutes before being filtered and ground. The powder was then washed in water (600 cm$^3$) for 30 minutes, filtered and ground, then re-washed in cold IPA. A NaOH wash followed (250 cm$^3$, 0.10 mol dm$^{-3}$) at 70° C. for 20 minutes. The solid was then macerated with a Silverson L5M in warm water (3.5 dm$^3$) for 40 minutes and filter-dried. This maceration was repeated three times. The final product was dried in vacuo at 40° C. The yield was around 120 g (0.17 mol), 88%. This synthesis procedure gave a molecular blend which has an average benzoxazine functionality of ~2.5 (functionality being defined as the average number of benzoxazine rings per molecule).

2. Multifunctional Benzoxazine—Method B 1,1,1-Tris(4-hydroxyphenyl)ethane (60.00 g, 0.20 mol), p-formaldehyde (37.2 g, 1.24 mol) and p-toluidine (66.00 g, 0.616 mol) were combined in a jar and placed in an oil bath. The jar was equipped with overhead stirring and the oil bath was heated to 85° C. Around this temperature an exothermic reaction occurs. The oil bath temperature was raised to 110° C. and held for 30 minutes. The temperature was then set to 130° C. and once the internal temperature of the resin reached 110° C. a 30 minute timer was started. After the 30 minutes was elapsed the molten mixture was poured onto release paper and allowed to cool. The solid was then crushed to a fine powder. The powder was washed twice in NaOH solution (700 cm$^3$, 1 mol dm$^{-3}$) at 70° C. The solid was washed with 700 cm$^3$ portions of distilled water at 70° C. until the water was pH7. The solid was then filtered and dried in vacuo at 40° C. The yield is about 120 g (0.17 mol), 88%. This synthesis procedure gave a molecule which has an average benzoxazine functionality of ~3.

3. Blend Preparation of a 70:30 Bis-A Benzoxazine:Multifunctional Benzoxazine

Bis-A benzoxazine (84 g) was added to multifunctional benzoxazine (36 g) then placed in an oil bath at 140° C. The benzoxazines were stirred via an overhead air stirrer. Once melted, the resin was stirred for 30 minutes. Following blending, 10-12 g of material was placed in a 60 mm diameter aluminium dish and/or 85-90 g was placed in a 6"×4" steel mould (to make plaques for mechanical and flexural modulus tests). Degassing took place in a Thermo-Scientific vacuum oven for approximately 3 hours at 120° C., depending on the viscosity of the system and vacuum strength.

4. Standard Cure Cycle for Benzoxazines

All benzoxazine samples were cured using a modified version of the cure cycle recommended by Huntsman: Starting temperature was 25° C. if resins were cured from cold or 100° C. if curing was completed on the same day as degassing. Start temperature −180° C. at 1° C. min$^{-1}$, held for 2 hr, 180° C. to 200° C. at 1° C. min$^{-1}$, held for 2 hr, 200° C. to 25° C. at 2° C. min$^{-1}$.

A number of different benzoxazine blends were prepared according to the weight % shown in Table 1.

TABLE 1

| Bis-A Benzoxazine: Multifunctional Benzoxazine | |
|---|---|
| % Bis-A BOX | % Multifunctional BOX |
| 100 | 0 |
| 95 | 5 |
| 90 | 10 |
| 80 | 20 |
| 70 | 30 |

FIG. 1 shows the MEK uptake in refluxing MEK of the multifunctional benzoxazine blends and Bis-A benzoxazine. Unless stated otherwise, all solvent uptake and density data are from blends utilising multifunctional benzoxazine were made via method A. The term "BOX" in the Tables and figures disclosed herein is an abbreviation for benzoxazine.

Resin specimens for the MEK uptake testing were ~40 mm long, 4 mm deep and 1.6 mm thick. The specimens were refluxed during the day in MEK solvent, cooled to ambient temperature and left at ambient temperature overnight and at weekends. The specimens were removed, air dried and weighed each morning, then placed back into the MEK and refluxed for the rest of the day. The graph in FIG. 1 shows the square root of the amount of time at reflux on the X-axis versus the MEK uptake (%) on the Y-axis. Note that in FIG. 1 the rate of uptake in the multifunctional benzoxazine-containing blends is significantly decreased.

The trace for Bis-A benzoxazine shows a fast MEK pickup compared to the other samples but then shows a weight loss of the specimen after ~36 h, this is due to sample degradation and cracking and the flaking off of material.

In terms of comparison, the times for a 3% MEK uptake in cured multifunctional-Bis-A benzoxazine blends are shown in Table 2.

TABLE 2

| Neat BOX based on Bis-A BOX | | |
|---|---|---|
| % Multifunctional BOX | Time to 3% MEK uptake (h) | Improvement factor |
| 0 | 9 | x |
| 5 | 75 | 8 |
| 10 | 92 | 10 |
| 20 | 144 | 16 |
| 30 | 232 | 26 |

Note the significant reduction in the rate of MEK pickup even with the addition of only 5% multifunctional benzoxazine.

Additional solvent uptake studies were therefore commissioned to examine the effect of 1-5% multifunctional-BOX addition. The data is shown in FIG. 2.

Figure 2:
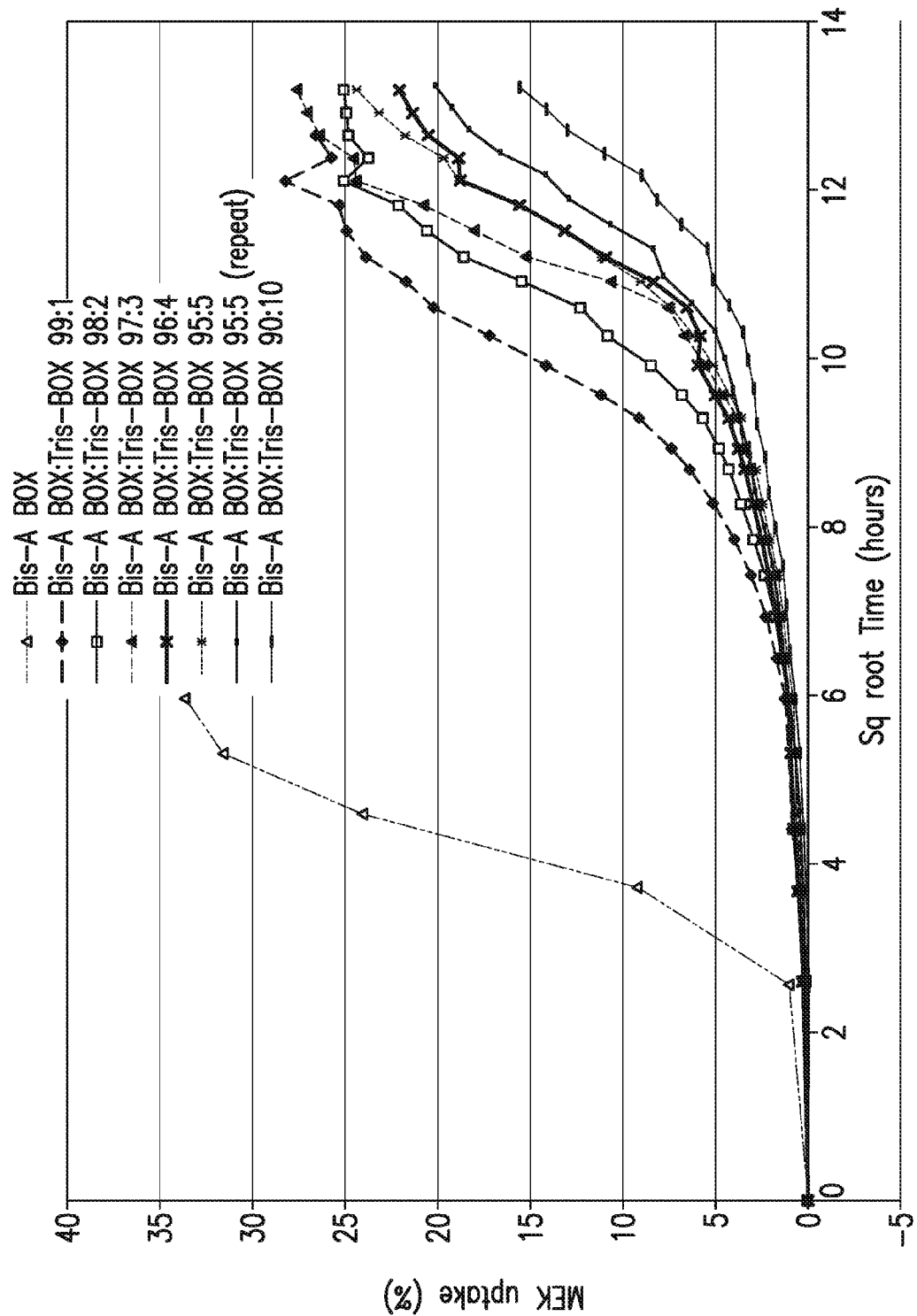
FIG. 2 shows the effect of multifunctional benzoxazine addition on the rate of solvent uptake for different benzoxazine blends prepared in an example.

FIG. 2 clearly shows that there is reduction in the rate of MEK uptake at even 1% multifunctional benzoxazine and that as the amount of multifunctional benzoxazine in the blend is increased the MEK uptake is slowed even further.

Figure 3:
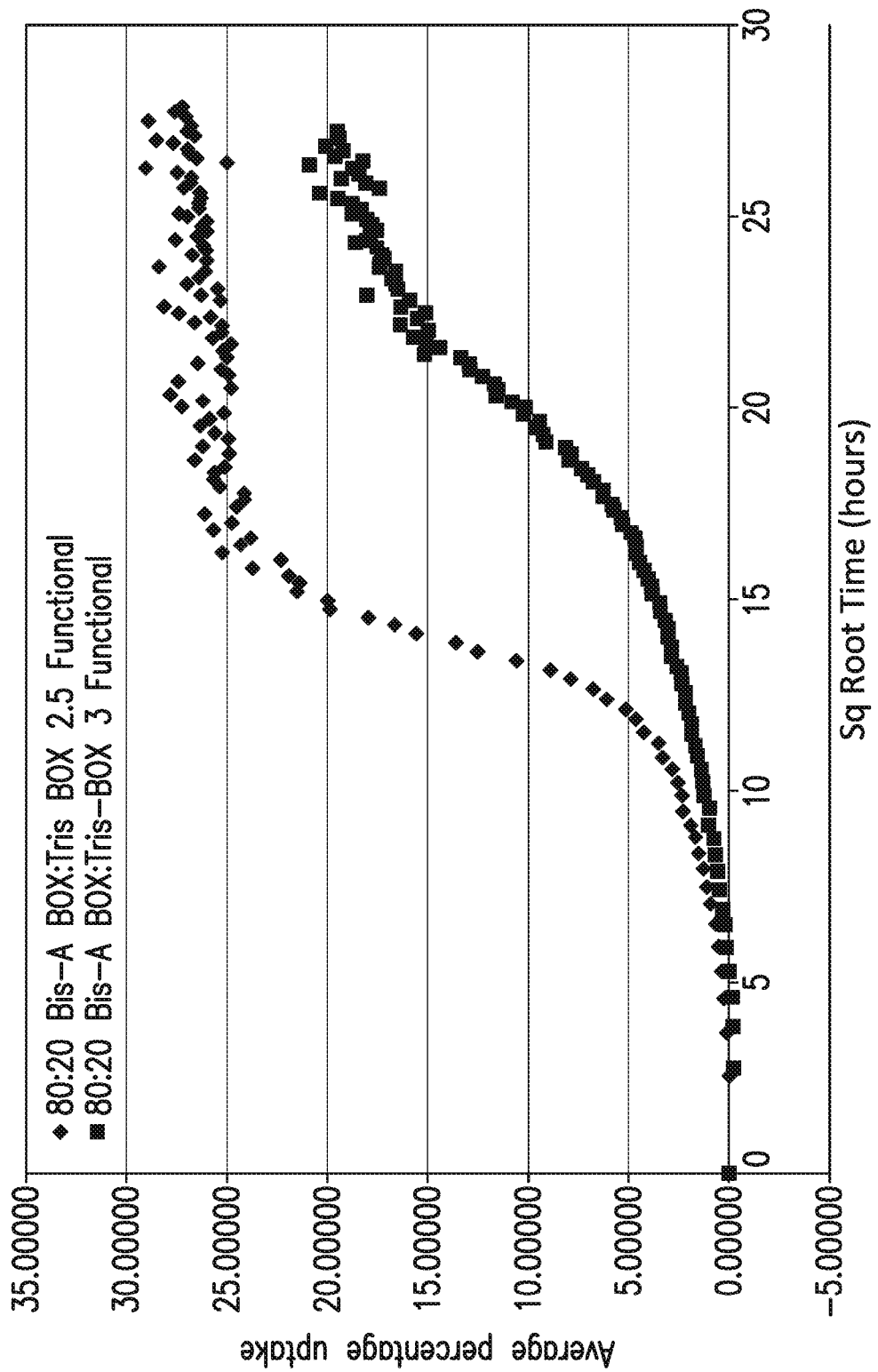
FIG. 3 shows the rate of solvent uptake of two different benzoxazine blends—one containing benzoxazine with average functionality of 2.5 and one containing benzoxazine with average functionality of 3.

A comparison of a blend of 80:20 ratio Bis-A-benzoxazine:multifunctional-benzoxazine with the multifunctional benzoxazine synthesized via either route A or route B is shown in FIG. 3. It can be seen from FIG. 3 that the multifunctional benzoxazine with average functionality of 3 is even more effective in retarding the rate of MEK uptake than multifunctional benzoxazine with average functionality of 2.

Figure 4:
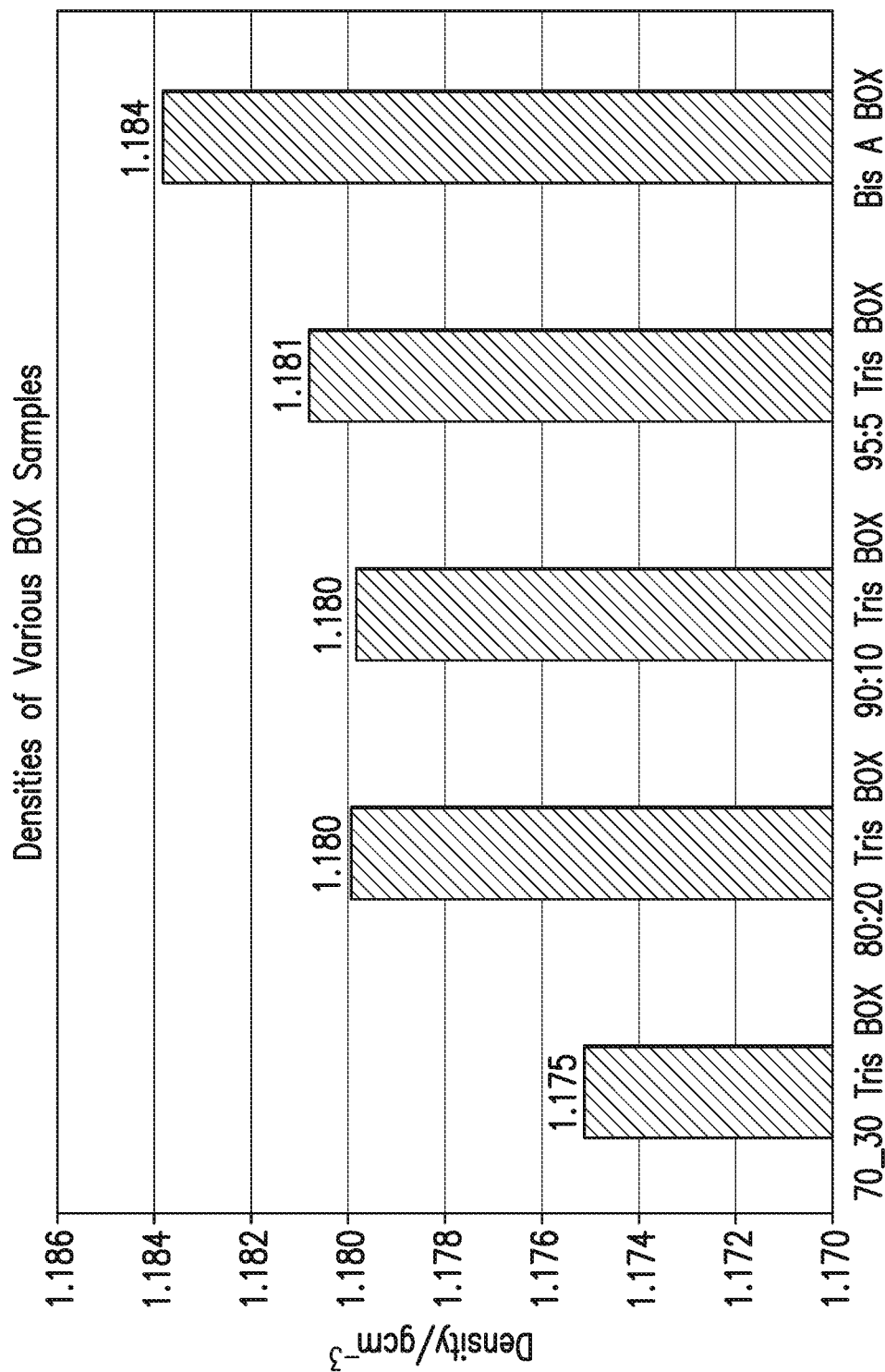
FIG. 4 shows the density measurements for various benzoxazine samples prepared in an example.

Density measurements of the multifunctional benzoxazine:Bis-A benzoxazine blends using a displacement technique are shown in FIG. 4. As can be seen, the greater the level of multifunctional benzoxazine, the less dense the material. Positron Annihilation Lifetime Spectrometry (PALS) measurements of "free volume" trends towards increasing with increasing multifunctional benzoxazine (see Table 3). It is surprising that the MEK uptake is reduced. What this suggests is that the possible mechanism by which the multifunctional benzoxazine functions is to retard the swelling of the resin by the MEK. Such swelling would facilitate MEK ingress.

TABLE 3

| Bis-A BOX: Multifunctional-BOX Ratio | Lifetime (ns) | Intensity (I) (%) | Diameter of free-volume hole (nm) | Volume (V) of free-volume hole ($nm^3$) | Free Volume (I*V) (% $nm^3$) |
|---|---|---|---|---|---|
| 100:0 | 1.773 ± 0.007 | 15.84 ± .15 | 0.521 ± .0014 | 0.0740 ± .0006 | 1.173 ± 0.015 |
| 95:5 | 1.776 ± 0.007 | 16.35 ± .11 | 0.522 ± .0014 | 0.0745 ± .0006 | 1.218 ± 0.015 |
| 90:10 | 1.807 ± 0.007 | 15.90 ± .15 | 0.528 ± .0014 | 0.0771 ± .0006 | 1.226 ± 0.015 |
| 80:20 | 1.799 ± 0.007 | 16.15 ± .16 | 0.527 ± .0014 | 0.0766 ± .0006 | 1.238 ± 0.015 |
| 70:30 | 1.799 ± 0.007 | 15.91 ± .16 | 0.527 ± .0014 | 0.0766 ± .0006 | 1.219 ± 0.015 |

Table 3 shows the results of positron annihilation spectroscopy on samples of the benzoxazine blends. Ratios shown are weight ratios. Samples sandwiched a weak $^{22}$Na positron source sealed in thin Kapton sheets that stop 5-10% of the positrons. Gamma detectors of the spectrometer detected annihilation events, this measured the lifetime of the positronium and the intensity of the positronium annihilation. This allowed calculation of the total free volume, hole size free volume and the average hole diameter. This gives a measure of density and molecular packing.

TABLE 4

| Bis-A BOX: Multifunctional BOX | Average functionality of multifunctional BOX | Tg (peak Tan delta, ° C.) |
|---|---|---|
| 100:0 | x | 182 |
| 90:10 | 2.5 | 189 |
| 90:10 | 3 | 189 |
| 80:20 | 2.5 | 194 |
| 80:20 | 3 | 191 |
| 70:30 | 2.5 | 197 |
| 70:30 | 3 | 193 |

Table 4 shows the $T_g$ measured by peak Tan delta. Note that $T_g$ is increased by up to 11° C. at 30% multifunctional benzoxazine.

What is claimed is:

1. A curable resin composition comprising more than 80% by weight of a benzoxazine blend, wherein the benzoxazine blend comprises: (A) a difunctional benzoxazine component; and (B) a multifunctional benzoxazine component with an average functionality of greater than 2, wherein component (B) comprises a tri-functional benzoxazine compound represented by the following structure I:

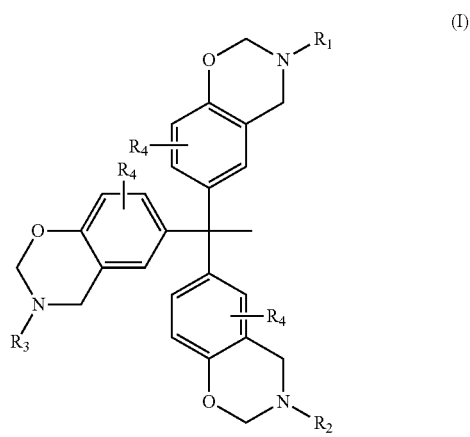

where $R_1$, $R_2$ and $R_3$ are independently selected from alkyl, cycloalkyl, and aryl, wherein the cycloalkyl and aryl groups are optionally substituted, and where substituted, one or more substituent groups may be present on each cycloalkyl and aryl group; and $R_4$ is selected from hydrogen, halogen, alkyl and alkenyl, wherein component (B) is a reaction product of trihydric phenol, aromatic amine and formaldehyde, and wherein the multifunctional benzoxazine component (B) is present in an amount up to 30% by weight based on the total weight of the benzoxazine blend in the composition.

2. The curable resin composition of claim 1, wherein upon curing of the resin composition to form a cured resin, the cured resin exhibits a slow rate of organic solvent uptake that is 5 times slower relative to the same cured resin without component (B).

3. A curable resin composition comprising more than 80% by weight of a benzoxazine blend, wherein the benzoxazine blend comprises: (A) a difunctional benzoxazine component; and (B) a multifunctional benzoxazine component with an average functionality of greater than 2, wherein component (B) comprises a tri-functional benzoxazine compound represented by the following structure II:

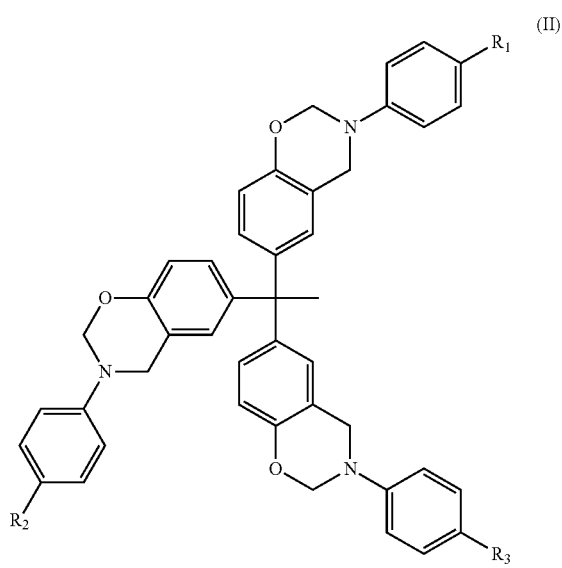

where $R_1$, $R_2$ and $R_3$ are alkyl, and wherein the multifunctional benzoxazine component (B) is present in an amount up to 30% by weight based on the total weight of the benzoxazine blend in the composition.

4. The curable resin composition of claim 3, wherein $R_1$, $R_2$ and $R_3$ of Structure II are independently selected from $C_{1-8}$ alkyl.

5. The curable resin composition of claim 4, wherein component (B) comprises a tri-functional benzoxazine represented by the following structure III:

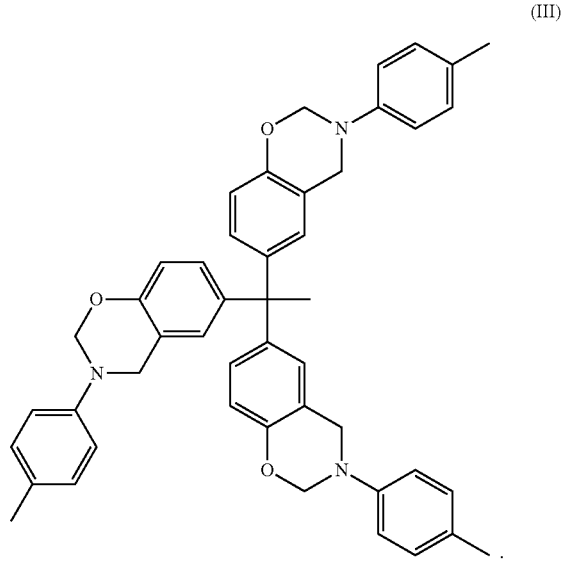 [SMILES: Cc1ccc(N2COc3ccc(C(C)(c4ccc5c(c4)CN(c4ccc(C)cc4)CO5)c4ccc5c(c4)CN(c4ccc(C)cc4)CO5)cc3C2)cc1]

6. The curable resin composition of claim 5, wherein component (B) is a reaction product of 1,1,1-Tris (4-hydroxyphenyl)ethane, p-toluidine and p-formaldehyde.

7. The curable resin composition of claim 3, wherein the weight ratio of multifunctional benzoxazine component (B) to difunctional benzoxazine component (A) is within the range of 1:99 to 30:70.

8. The curable resin composition of claim 3, wherein component (B) is a reaction product of trihydric phenol, aromatic amine and formaldehyde.

9. The curable resin composition according to claim 3, wherein the difunctional benzoxazine is represented by the following structure (IV):

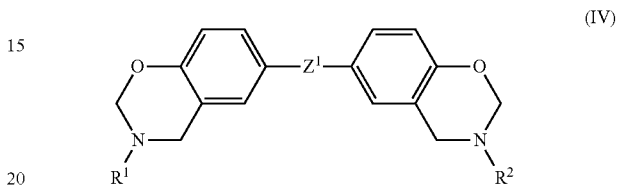

where:

$Z^1$ is selected from a direct bond, —C($R^3$)($R^4$)—, —C($R^3$)(aryl)-, —C(O)—, —S—, —O—, —S(O)—, —S(O)$_2$—, a divalent heterocycle and —[C($R^3$)($R^4$)]$_x$-arylene-[C($R^5$)($R^6$)]$_y$—, or the two benzyl rings of the benzoxazine moieties may be fused; and $R^1$ and $R^2$ are independently selected from alkyl, cycloalkyl, and aryl, wherein the cycloalkyl and aryl groups are optionally substituted by a substituent selected from: $C_{1-8}$ alkyl, halogen and amine groups, and where substituted, one or more substituent groups may be present on each cycloalkyl and aryl group;

$R^3$, $R^4$, $R^5$ and $R^6$ are independently selected from H, $C_{1-8}$ alkyl, and halogenated alkyl; and x and y are independently 0 or 1.

10. The curable resin composition according to claim 3, wherein the di-functional benzoxazine is represented by the following structure V:

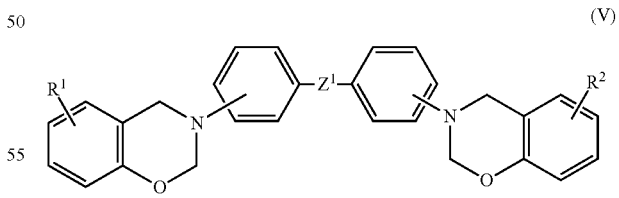

where:

$Z^1$ is selected from a direct bond, —C($R^3$)($R^4$)—, —C($R^3$)(aryl)-, —C(O)—, —S—, —O—, —S(O)—, —S(O)$_2$—, a divalent heterocycle and —[C($R^3$)($R^4$)]$_x$-arylene-[C($R^5$)($R^6$)]$_y$—, or the two benzyl rings may be fused; and R¹ and R² are independently selected from hydrogen, alkyl, cycloalkyl and aryl, wherein the cycloalkyl and aryl groups are optionally substituted by a substituent selected from: $C_{1-8}$ alkyl, halogen and amine groups, and where substituted, one or more substituent groups may be present on each cycloalkyl and aryl group;

R³, R⁴, R⁵ and R⁶ are independently selected from H, $C_{1-8}$ alkyl, and halogenated alkyl; and x and y are independently 0 or 1.

11. The curable resin composition of claim 3, wherein the curable composition is void of or contains less than 5% by weight, based on the total weight of the composition, of any thermosettable resin selected from epoxy, cyanate ester, bismaleimide, and phenol-formaldehyde.

12. A composite material comprising reinforcement fibers impregnated or infused with the curable composition according to claim 3.

13. The composite material of claim 12, wherein the reinforcement fibers are selected from carbon fibers, glass fibers, and aramid fibers.

14. The composite material of claim 12, wherein the reinforcement fibers are in the form of unidirectional fibers, a fabric, or a preform comprising multiple layers of fibers or fabric plies.

15. A curable resin composition comprising more than 80% by weight of a benzoxazine blend, wherein the benzoxazine blend comprises: (A) a difunctional benzoxazine component; and (B) a multifunctional benzoxazine component with an average functionality of greater than 2 and up to 3, wherein component (B) is a reaction product of trihydric phenol, aromatic amine and formaldehyde, and the trihydric phenol is represented by the following structure:

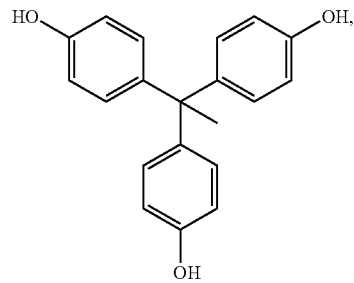

and component (B) is present in an amount up to 30% by weight based on the total weight of the benzoxazine blend in the composition.

16. The curable resin composition of claim 15, wherein component (B) is a reaction product of 1,1,1-Tris (4-hydroxyphenyl)ethane, p-toluidine and p-formaldehyde.

17. The curable resin composition of claim 15, wherein the weight ratio of component (B) to component (A) is within the range of 1:99 to 30:70.

18. The curable resin composition according to claim 15, wherein the curable composition is void of or contains less than 5% by weight, based on the total weight of the composition, of any thermosettable resin selected from epoxy, cyanate ester, bismaleimide, and phenol-formaldehyde.

19. A cured composite part produced from a method comprising: (i) impregnating or infusing reinforcement fibers with the curable composition according to claim 1; and (ii) curing the impregnated or infused fibers.

* * * * *